(12) United States Patent
Fitzpatrick et al.

(10) Patent No.: US 10,898,675 B2
(45) Date of Patent: Jan. 26, 2021

(54) URINARY CATHETERS HAVING LIMITED REUSABILITY

(71) Applicant: Hollister Incorporated, Libertyville, IL (US)

(72) Inventors: James J. Fitzpatrick, Ballina (IE); Adam J. Foley, Swords (IE); Padraig M. O'Flynn, Ballina (IE); John T. Clarke, Galway (IE); Paul C. Fletter, Mount Prospect, IL (US); William K. Arnold, Gurnee, IL (US)

(73) Assignee: Hollister Incorporated, Libertyville, IL (US)

( * ) Notice: Subject to any disclaimer, the term of this patent is extended or adjusted under 35 U.S.C. 154(b) by 772 days.

(21) Appl. No.: 15/565,683

(22) PCT Filed: Apr. 19, 2016

(86) PCT No.: PCT/US2016/028230
§ 371 (c)(1),
(2) Date: Oct. 11, 2017

(87) PCT Pub. No.: WO2016/204858
PCT Pub. Date: Dec. 22, 2016

(65) Prior Publication Data
US 2018/0071482 A1 Mar. 15, 2018

Related U.S. Application Data

(60) Provisional application No. 62/175,525, filed on Jun. 15, 2015.

(51) Int. Cl.
A61M 25/00 (2006.01)

(52) U.S. Cl.
CPC .... *A61M 25/0017* (2013.01); *A61M 25/0009* (2013.01); *A61M 2025/0019* (2013.01);
(Continued)

(58) Field of Classification Search
CPC .......... A61M 25/0017; A61M 25/0009; A61M 2025/0019; A61M 2025/0056;
(Continued)

(56) References Cited

U.S. PATENT DOCUMENTS

| 4,721,123 A | 1/1988 | Cosentino et al. |
| 1,955,978 A | 3/1993 | Schiffer |

(Continued)

FOREIGN PATENT DOCUMENTS

| DE | 10 2007 011 220 B3 | 1/2008 |
| WO | WO 95/32755 A1 | 12/1995 |

(Continued)

OTHER PUBLICATIONS

International Search Report and Written Opinion for PCT/US2016/028230 dated Jul. 27, 2016.

*Primary Examiner* — Andrew J Mensh
(74) *Attorney, Agent, or Firm* — Cook Alex Ltd.

(57) ABSTRACT

A reusable urinary catheter assembly includes a catheter shaft and a plurality of removable members associated with the catheter shaft. A different one of the removable members is configured to be removed from the catheter shaft between each consecutive use of the reusable urinary catheter assembly. By such a configuration, the number of times that the reusable urinary catheter may be reused is limited by the number of removable members.

20 Claims, 3 Drawing Sheets

(52) U.S. Cl.
CPC ............. *A61M 2025/0056* (2013.01); *A61M 2025/0078* (2013.01); *A61M 2205/276* (2013.01); *A61M 2210/1085* (2013.01)

(58) Field of Classification Search
CPC .... A61M 2025/0078; A61M 2205/276; A61M 2210/1085
USPC ....................................................... 604/544
See application file for complete search history.

(56) References Cited

U.S. PATENT DOCUMENTS

| | | | |
|---|---|---|---|
| 5,209,726 A | | 5/1993 | Goosen |
| 5,409,469 A | | 4/1995 | Schaerf |
| 5,429,620 A | | 7/1995 | Davis |
| 5,507,731 A | * | 4/1996 | Hernandez ............ A61M 25/00 604/264 |
| 5,713,867 A | | 2/1998 | Morris |
| 5,944,695 A | | 8/1999 | Johnson et al. |
| 7,662,146 B2 | | 2/2010 | House |
| 7,766,394 B2 | | 8/2010 | Sage et al. |
| 7,789,873 B2 | * | 9/2010 | Kubalak ............ A61M 25/0111 604/544 |
| 8,016,799 B2 | | 9/2011 | Nash et al. |
| 8,124,446 B2 | | 2/2012 | Lee et al. |
| 8,252,247 B2 | | 8/2012 | Ferlic |
| 8,298,189 B2 | | 10/2012 | Fisher et al. |
| 8,311,633 B2 | | 11/2012 | Ransbury et al. |
| 8,317,775 B2 | | 11/2012 | House |
| 8,398,610 B2 | | 3/2013 | Locsin et al. |
| 8,454,564 B2 | | 6/2013 | Deppisch et al. |
| 8,808,273 B2 | | 8/2014 | Caples et al. |
| 8,888,747 B2 | | 11/2014 | House |
| 2008/0015527 A1 | | 1/2008 | House |
| 2008/0097411 A1 | | 4/2008 | House |
| 2008/0172042 A1 | | 7/2008 | House |
| 2008/0183038 A1 | * | 7/2008 | Tilson .................... A61B 1/018 600/104 |
| 2010/0049165 A1 | | 2/2010 | Sutherland et al. |
| 2012/0289942 A1 | | 11/2012 | Becker et al. |
| 2013/0138087 A1 | | 5/2013 | Chung |
| 2013/0231639 A1 | | 9/2013 | Tatlow |
| 2014/0276661 A1 | | 9/2014 | Hannon et al. |
| 2015/0320970 A1 | * | 11/2015 | Foley ................ A61M 25/0054 604/544 |
| 2017/0056622 A1 | * | 3/2017 | O'Flynn ........... A61M 25/0017 |
| 2017/0209022 A1 | * | 7/2017 | Molnar ............. A61M 16/0465 |

FOREIGN PATENT DOCUMENTS

| | | |
|---|---|---|
| WO | WO 96/00099 A1 | 1/1996 |
| WO | WO 98/06642 A1 | 2/1998 |
| WO | WO 2015/084923 A1 | 6/2015 |

* cited by examiner

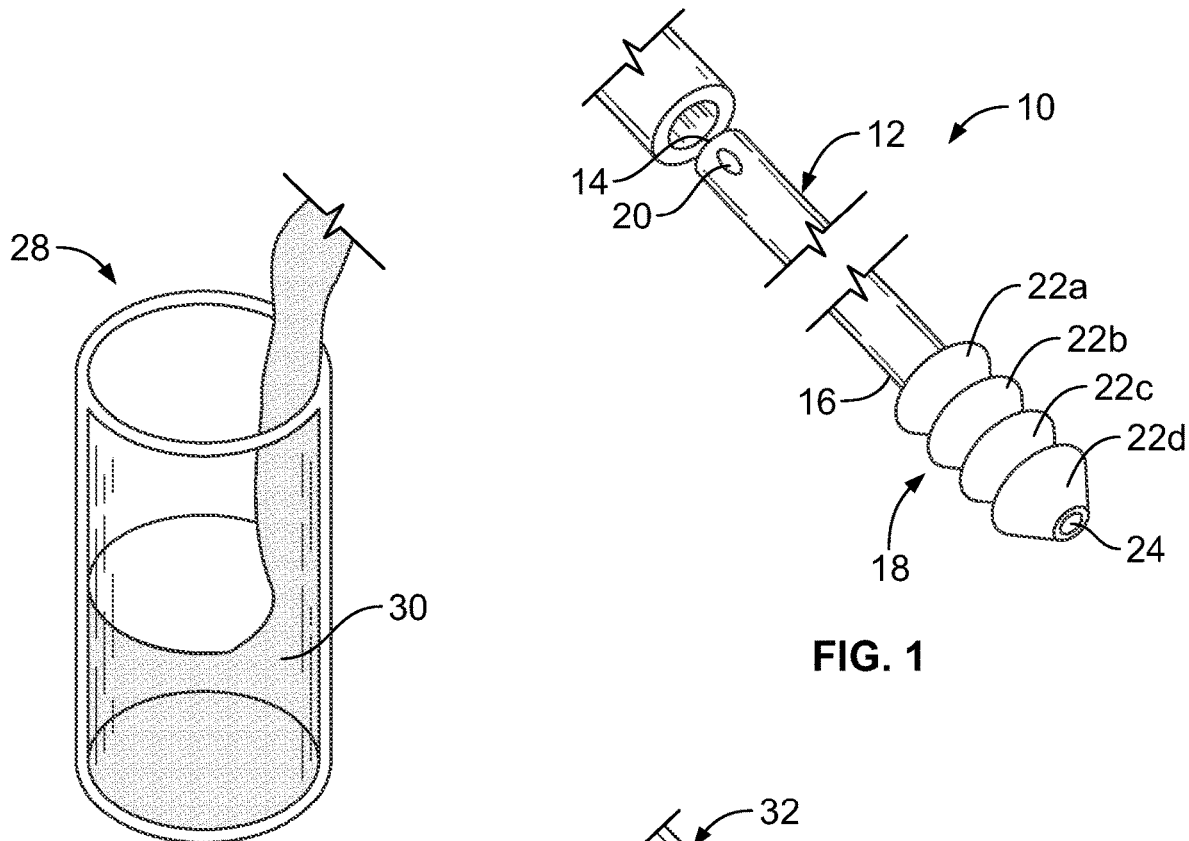
FIG. 1
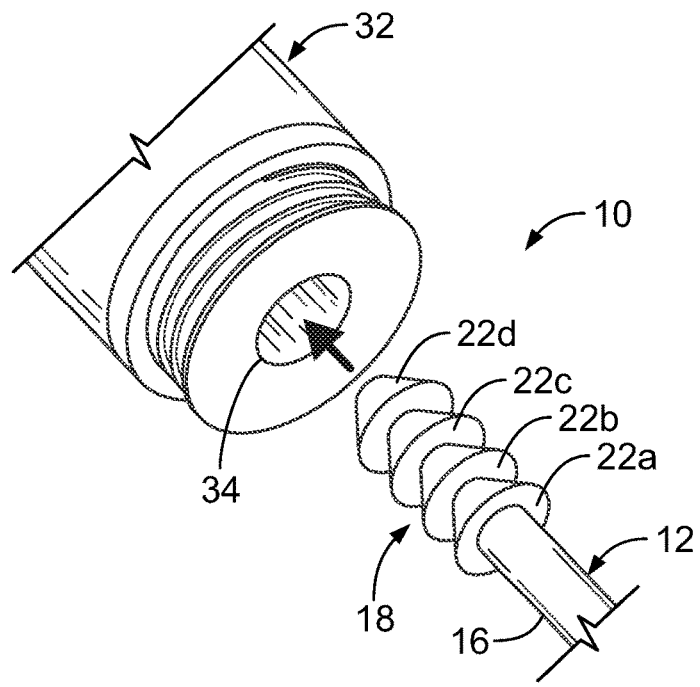
FIG. 2
FIG. 3

URINARY CATHETERS HAVING LIMITED REUSABILITY

RELATED APPLICATIONS

This application is a U.S. national stage application of PCT Patent Application Serial No. PCT/US2016/028230, filed Apr. 19, 2016, which claims the benefit of and priority of U.S. Provisional Patent Application Ser. No. 62/175,525, filed Jun. 15, 2015, the contents of which are incorporated by reference herein.

DESCRIPTION

Technical Field

The present disclosure generally relates to reusable urinary catheter assemblies. More particularly, the present disclosure relates to reusable urinary catheter assemblies that may be reused only a limited number of times.

Background

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary incontinence. With the advent of intermittent catheters, individuals with urinary system abnormalities can self-insert and self-remove intermittent catheters several times a day. Such catheters typically include a shaft that is sufficiently flexible to navigate the curves of the urethra (especially catheters intended for male users), yet rigid enough to be pushed through the urethra without collapsing or "snaking" before an end of the catheter reaches the bladder.

Two types of urinary catheters are single-use catheters and multi-use, reusable catheters. A single-use catheter is used once for catheterization and then disposed of after use, typically by being placed into a waste receptacle, such as a garbage can. A reusable catheter may be used for catheterization and then re-sterilized or otherwise reconditioned for sterile usage and then used a second time. There is no limit on the number of times that a reusable catheter may be re-sterilized and reused, although repeated use of a reusable catheter may degrade the integrity of the catheter (through repeated exposure to a sterilizing solution, urine, and other bodily fluids), such that it may be advantageous to limit the number of times that a catheter may be reused. Instructions may be provided with a reusable catheter to instruct a user as to the maximum recommended number of times that the catheter is to be reused, but such instructions will not necessarily be followed, and it would be advantageous to provide more affirmative means for limiting the number of times that a catheter may be reused.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a reusable urinary catheter assembly includes a catheter shaft and a plurality of removable members associated with the catheter shaft. A different one of the removable members is configured to be removed from the catheter shaft between each consecutive use of the reusable urinary catheter assembly, such that the number of times that the reusable urinary catheter assembly may be reused is limited by the number of removable members.

In another aspect, a method is provided for using a reusable urinary catheter assembly. According to the method, a reusable urinary catheter assembly is used for catheterization. A removable member is removed from the reusable urinary catheter assembly and the reusable urinary catheter assembly may be reused for catheterization. The steps of removing a removable member and reusing the reusable urinary catheter member are repeated a number of times that is limited by the number of removable members associated with the reusable urinary catheter assembly.

In yet another aspect, a reusable urinary catheter assembly includes a catheter shaft and a frangible drainage member. The catheter shaft extends between proximal and distal ends, with the frangible drainage member associated with the distal end of the catheter shaft. The frangible drainage member includes a plurality of segments, which are arranged from a proximal-most segment to a distal-most segment. At least the distal-most segment is a removable member, which is configured to be removed from the catheter shaft between consecutive uses of the reusable urinary catheter assembly.

In another aspect, a reusable urinary catheter assembly includes a catheter shaft and a plurality of concentric cover layers. The catheter shaft has an outer surface, with the cover layers being arranged from an innermost cover layer associated with the outer surface of the catheter shaft to an outermost cover layer. At least the outermost cover layer is a removable member configured to be removed from the catheter shaft between consecutive uses of the reusable urinary catheter assembly.

BRIEF DESCRIPTION OF THE DRAWINGS

FIG. 1 is a perspective view of a reusable urinary catheter assembly according to an aspect of the present disclosure;

FIG. 2 is a perspective view of a storage container for the reusable urinary catheter assembly of FIG. 1;

FIG. 3 is a bottom perspective view of a lid of the storage container of FIG. 1;

Figure 4:
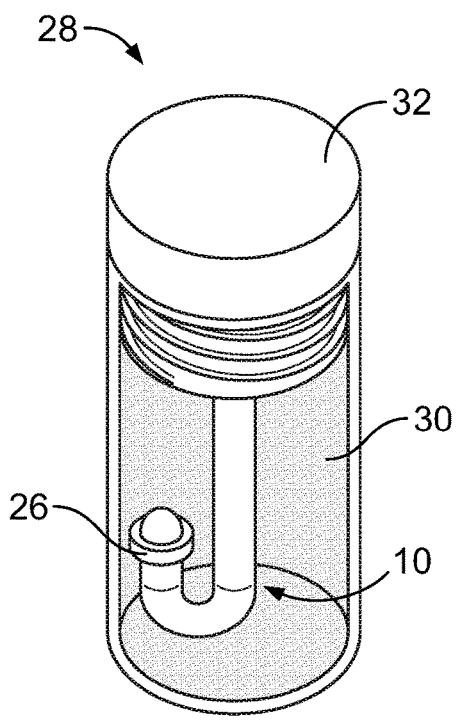
FIG. 4 is a perspective view of the storage container and lid of FIGS. 2 and 3, with the reusable urinary catheter assembly of FIG. 1 positioned within the storage container.

DETAILED DESCRIPTION OF THE
ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

FIG. 1 shows a reusable urinary catheter assembly 10 according to the present disclosure. The reusable urinary catheter assembly 10 may be provided as either a male catheter assembly or as a female catheter assembly without departing from the scope of the present disclosure.

The reusable urinary catheter assembly 10 includes a catheter shaft 12, which may be provided as an elongated, hollow tube extending between a closed proximal end 14 and an open distal end 16, with a frangible drainage member 18 associated with the distal end 16 of the catheter shaft 12. The catheter shaft 12 may include one or more drainage eyes or openings 20 at or adjacent to the proximal end 14 of the catheter shaft 12 to drain urine from a bladder into the hollow interior of the catheter shaft 12, where it flows to the frangible drainage member 18 to exit the reusable urinary catheter assembly 10 (as will be described in greater detail). The catheter shaft 12 may be made of any suitable material (e.g., polyvinyl chloride or some other material, such as silicone), which may vary depending on the desired characteristics of the catheter shaft 12 (e.g., stiffness). The catheter shaft 12 may also be provided in any of a number of sizes, including length and gauge or diameter (e.g., 6, 8, 10, 12, 14, 16, 18, or 20 Ch).

The frangible drainage member 18 is configured to provide the reusable urinary catheter assembly 10 with added functionality that limits the number of times that the reusable urinary catheter assembly 10 may be reused. In particular, the frangible drainage member 18 is defined by a plurality of segments 22a-22d, which are arranged end-to-end from a proximal-most segment 22a to a distal-most segment 22d. The illustrated embodiment is provided with four segments 22a-22d, but it is within the scope of the present disclosure for the frangible drainage member 18 to include more or fewer than four segments. Preferably, the frangible drainage member 18 includes at least two segments. Regardless of the number of segments, each includes a through-hole or fluid passage 24, which is in fluid communication with the hollow interior of the catheter shaft 12 to allow urine in the catheter shaft 12 to flow through the frangible drainage member 18 to exit the reusable urinary catheter assembly 10. The diameter of the through-hole 24 may be greater than, less than, or substantially equal to the diameter of the hollow interior of the catheter shaft 12.

In the illustrated embodiment, the segments 22a-22d are substantially identical, each being generally frusto-conical. The illustrated frusto-conical segments 22a-22d are arranged end-to-end, with the larger end of each segment positioned proximally of the smaller end of that segment. The smaller, distal end of each segment is associated with the larger, proximal end of the adjacent distal segment, while the larger, proximal end of each segment is associated with the smaller, distal end of the adjacent proximal segment. It should be understood that the shape of the segments shown in FIG. 1 is merely exemplary and that differently shaped segments may be provided without departing from the scope of the present disclosure. Additionally, the various segments of an individual frangible drainage member may be differently configured from each other (e.g., being the same shape, but differently sized) without departing from the scope of the present disclosure.

At least the distal-most segment 22d is a removable member, which may be removed from the catheter shaft 12 and from the remainder of the frangible drainage member 18. Preferably, all but the proximal-most segment 22a are removable members (with the proximal-most segment 22 being fixedly secured to the catheter shaft 12 at or adjacent to the distal end 16 of the catheter shaft 12), but it is also within the scope of the present disclosure for the proximal-most segment 22a to be a removable member. It may also be preferred for the removable segments to be configured to be individually removed, although it is also within the scope of the present disclosure for the removable segments to be configured such that multiple segments are removed simultaneously.

In one embodiment, the removable segments may be removed by applying a distally directed force thereto to break the most distal removable segment apart from the adjacent proximal segment, but it is also within the scope of the present disclosure for a different mechanism to be employed to separate a removable segment. For example, a removable segment may be removed by applying a torsional force to it or by applying a shearing force to it or by applying a combination of forces. In a preferred embodiment, the removable segments are configured to be removed by the same mechanism (e.g., each being removed by a distally directed force), but it is within the scope of the present disclosure for two segments of the same frangible drainage member 18 to be removed by different mechanisms.

In one embodiment, each of the removable segments is configured to be removed using substantially the same amount of force. However, in a more preferred embodiment, the amount of force required to remove at least two of the removable segments (and even more preferably the amount of force required to remove each of the removable segments) is different. If the removable segments are configured to be removed at different applied forces, it may be advantageous for the force required to remove each successive removable segment (i.e., from the most distal removable segment to the most proximal removable segment) to increase. Thus, the force required to remove segment 22d would be less than the force required to remove segment 22c, which would be less than the force required to remove segment 22b. Such a configuration better ensures that removing the current distal-most removable segment does not also remove the adjacent proximal removable segment, thus allowing the removable segments to be individually removed.

In use, a user may begin by removing the reusable urinary catheter assembly 10 from a sealed package (if provided). With the reusable urinary catheter assembly 10 outside of the package, the user may grip the frangible drainage member 18 and use it to orient the proximal end 14 of the catheter shaft 12 adjacent to the urethral opening. In one embodiment, the proximal end 14 of the catheter shaft 12 may be provided with an introducer tip 26 (FIG. 4) according to conventional design, which encircles the proximal end 14 of the catheter shaft 12. If provided, a portion of the introducer tip 26 (e.g., a flange having a relatively large diameter) may be gripped instead of or in addition to gripping the frangible drainage member 18 to properly orient the proximal end 14 of the catheter shaft 12. A proximal end of the introducer tip 26 may be advanced into the urethra, with the catheter shaft 12 then being moved proximally with respect to the introducer tip 26 (e.g., by gripping the frangible drainage member 18 and moving it proximally) to advance the proximal end 14 of the catheter shaft 12 out of the proximal end of the introducer tip 26 and into the urethra.

The user continues advancing the proximal end 14 of the catheter shaft 12 through the urethra until the proximal end 14 is positioned within the bladder, with at least the frangible drainage member 18 positioned outside of the urethra. So positioning the reusable urinary catheter assembly 10 causes urine in the bladder to drain into the catheter shaft 12 via the drainage eye(s) 20. The urine flows from the proximal end 14 of the catheter shaft 12, through the hollow interior, and to the distal end 16 of the catheter shaft 12. The urine flows from the distal end 16 of the catheter shaft 12 and into the through-hole 24 of the frangible drainage member 18, where it exits the reusable urinary catheter assembly 10. The urine may be directed into a toilet or other waste receptacle (e.g., a waste bag secured to or otherwise associated with the frangible drainage member 18).

After the reusable urinary catheter assembly 10 has been used to drain urine from the bladder, the user may grip the frangible drainage member 18 and move it distally away from the body to withdraw the catheter shaft 12 from the urethra. The reusable urinary catheter assembly 10 may then be re-sterilized or otherwise reconditioned for reuse. Prior to the reusable urinary catheter assembly 10 being used a second time, the proximal-most removable segment 22d is removed. This removable segment 22d may be removed before or after re-sterilizing the reusable urinary catheter assembly 10. The steps of using the reusable urinary catheter assembly 10 for catheterization, re-sterilization or reconditioning of the reusable urinary catheter assembly 10, and removal of one or more of the removable segments may be repeated until the final removable segment is removed. The reusable urinary catheter assembly 10 may be configured such that, when the final removable segment has been removed, the reusable urinary catheter assembly 10 may be used one last time before being replaced with another reusable urinary catheter assembly. Alternatively, the reusable urinary catheter assembly 10 may be configured such that, when the final removable segment has been removed, the reusable urinary catheter assembly 10 is no longer in condition for reuse or is otherwise ready for replacement with another reusable urinary catheter assembly.

Finally, the reusable urinary catheter assembly 10 may be disposed of (e.g., placed into a toilet if it is formed of a water-degradable material or otherwise placed into a garbage receptacle).

According to a preferred embodiment, between consecutive uses of the reusable urinary catheter assembly 10, the reusable urinary catheter assembly 10 is re-sterilized by placing it into a storage container 28 (FIG. 2) containing an amount of a sterilizing solution 30. The storage container 28 is provided with a lid 32 (FIG. 3) having a cavity 34 defined in its lower surface. Prior to placing the reusable urinary catheter assembly 10 into the sterilizing solution 30, the distal-most segment 22d is pressed into the cavity 34, as illustrated in FIG. 3. Preferably, the diameter of the opening into the cavity 34 is nominally smaller than the maximum diameter of the segments 22a-22d, with either the cavity opening or a segment deforming slightly to allow the segment to be pressed into the cavity 34. Providing a relatively small cavity opening allows the cavity 34 to retain a segment pressed into the cavity 34, such that attaching the lid 32 to the storage container 28 causes the reusable urinary catheter assembly 10 to be suspended from the lid 32 in the sterilizing solution 30 in the storage container 28, as shown in FIG. 4.

In other embodiments, rather than employing a sterilizing solution to recondition the reusable catheter assembly 10 for a second use, other re-sterilization methods may be employed. For example, in one embodiment, the reusable catheter assembly 10 may be steam sterilized between uses, using an autoclave or the like. These alternative sterilization approaches may be employed independently or in combination with the storage container 28. If an alternative sterilization approach is used, then the storage container 28 may either include or omit the sterilizing solution 30. If the sterilizing solution 30 is omitted, then the storage container 28 may either be empty or filled with some other fluid (e.g., a lubricating fluid).

Figure 5:
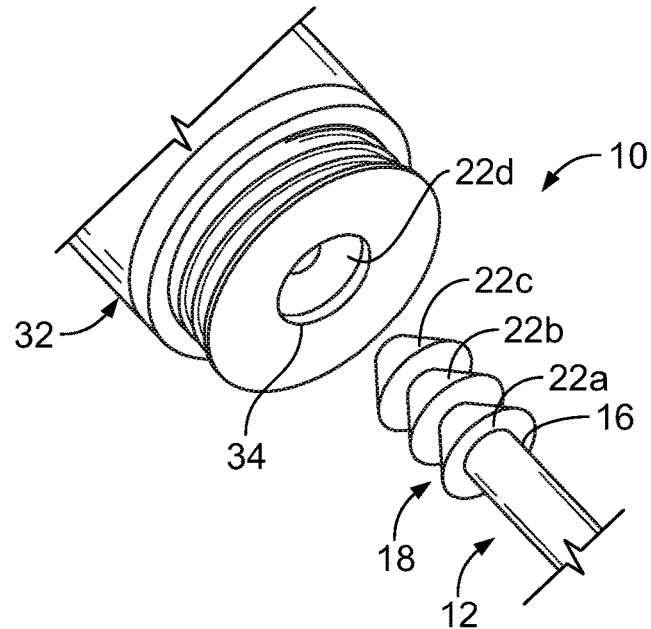
FIG. 5 is a bottom perspective view of the lid of FIG. 3 and the reusable urinary catheter assembly of FIG. 1, with the reusable urinary catheter assembly having been withdrawn from the lid to remove a removable member of the reusable urinary catheter assembly.

When the reusable urinary catheter assembly 10 is to be used a second time, the lid 32 is removed from the storage container 28 (or other sterilization device or storage location), thereby removing the reusable urinary catheter assembly 10 from the sterilizing solution 30 (if present within the storage container 28). The reusable urinary catheter assembly 10 is then moved away from the lid 32. As described above, a segment positioned within the cavity 34 is retained or trapped therein (due to the relatively small size of the cavity opening), such that moving the reusable urinary catheter assembly 10 away from the lid 32 with sufficient force causes the distal-most removable segment 22d to break off from the remainder of the frangible drainage member 18 and be retained in the lid cavity 34 (FIG. 5). With segment 22d so removed, the adjacent proximal segment 22c becomes the distal-most segment, and the reusable urinary catheter assembly 10 may be used a second time for catheterization (in the manner described above).

Figure 6:
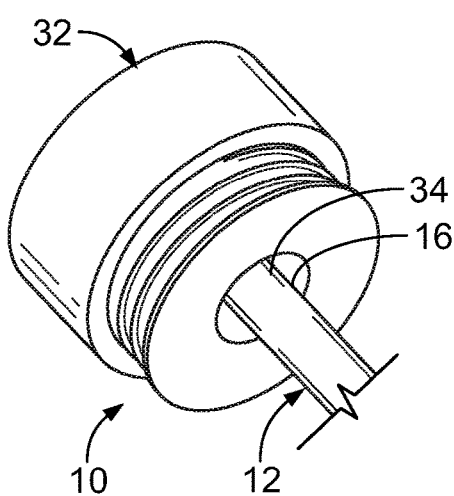
FIG. 6 is a bottom perspective view of the lid of FIG. 3 and the reusable urinary catheter assembly of FIG. 1, with a distal end of the reusable urinary catheter assembly irremovably received within the lid.

After using the reusable urinary catheter assembly 10 a second time, it is re-sterilized and the distal-most segment 22c is removed (as described above), leaving segment 22b as the distal-most segment. The reusable urinary catheter assembly 10 may then be used a third time for catheterization (as described above), followed by the reusable urinary catheter assembly 10 being re-sterilized. Following re-sterilization, the reusable urinary catheter assembly 10 is separated from the lid 32, thereby removing the distal-most segment 22b (as described above) and leaving only the proximal-most segment 22a. With only the proximal-most segment 22a remaining, the reusable urinary catheter assembly 10 is used yet again and re-sterilized (as described above). In a preferred embodiment, segment 22b is the final removable segment, with the proximal-most segment 22a being fixedly secured to the catheter shaft 12. Should the user attempt to remove the reusable urinary catheter assembly 10 from the storage container 28 for further use, they will find that the proximal-most segment 22a is trapped within the lid cavity 34 (FIG. 6), thereby preventing further use of the reusable urinary catheter assembly 10. Thus, it will be seen that the number of times that the reusable urinary catheter assembly 10 may be reused is limited by the number of removable segments. The number of times that a reusable urinary catheter assembly may be reused may be varied by providing it with differing numbers of removable members.

Figure 7:
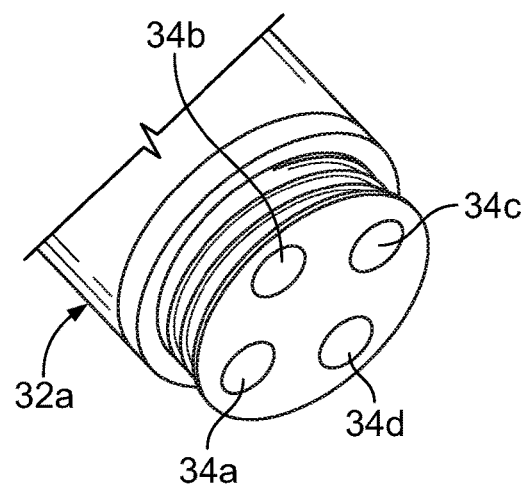
FIG. 7 is a bottom perspective view of an alternative embodiment of a lid that may be used in combination with the reusable urinary catheter assembly of FIG. 1 and the storage container of FIG. 2.

It should be understood that the illustrated embodiment of FIGS. 1-6 is merely exemplary and that variations to that design may be made without departing from the scope of the present disclosure. For example, in the embodiment of FIGS. 1-6, the lid 32 has only a single cavity 34, with each segment eventually being pressed into the cavity 34. In an alternative embodiment (FIG. 7), a plurality of cavities 34a-34d may be defined in the underside of the lid 32a, with the lid 32a preferably including one cavity for each segment of the frangible drainage member of a reusable urinary catheter assembly to be used in combination with the lid 32a. By such a configuration, each segment may be pressed into its own lid cavity, rather than all of the segments being consecutively advanced into a single lid cavity. This may allow for greater variation in the configuration of the segments, such as configuring each segment differently (e.g., with each being a different size), and with each lid cavity being configured to receive and retain only the segment having the corresponding size and shape. The segments and lid cavities may be color-coded to allow a user to more easily identify the cavity in which to insert each segment. Other variations to the configuration of the reusable urinary catheter assembly and associated components (e.g., the size, material composition, and configuration of the storage container and lid) may also be practiced without departing from the scope of the present disclosure.

Figure 8:
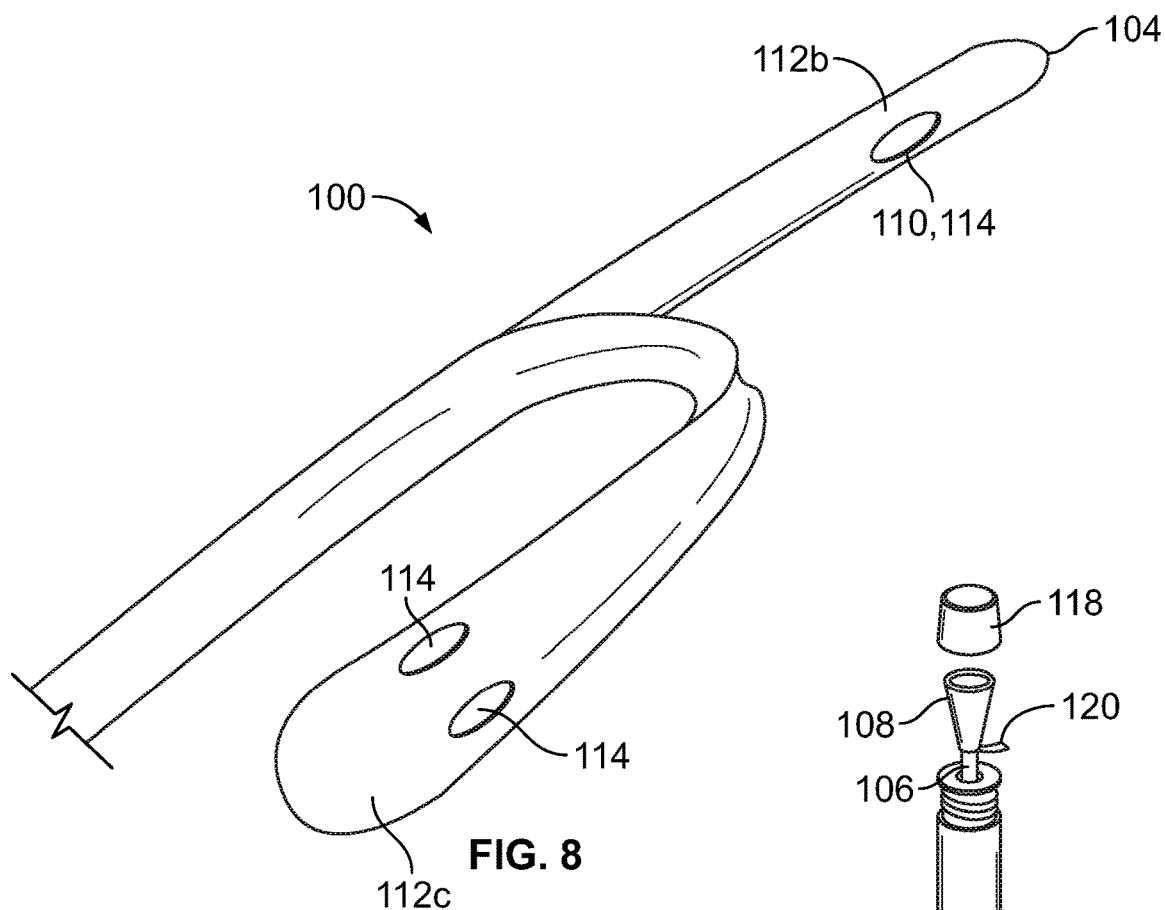
FIG. 8 is a perspective view of another embodiment of a reusable urinary catheter assembly according to the present disclosure.
Figure 9:
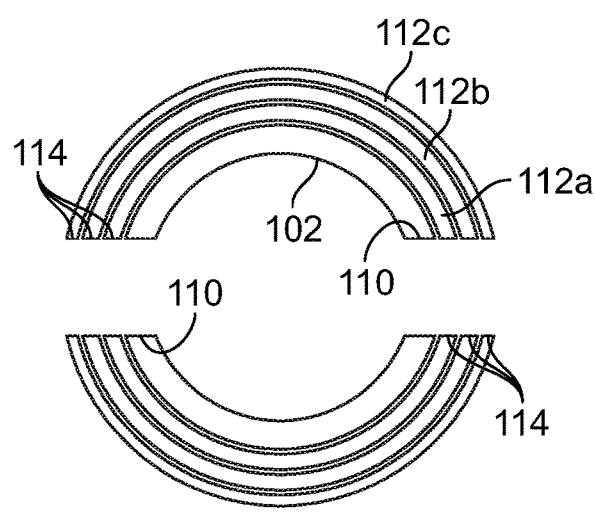
FIG. 9 is a cross-sectional view of the reusable urinary catheter assembly of FIG. 8.
Figure 10:
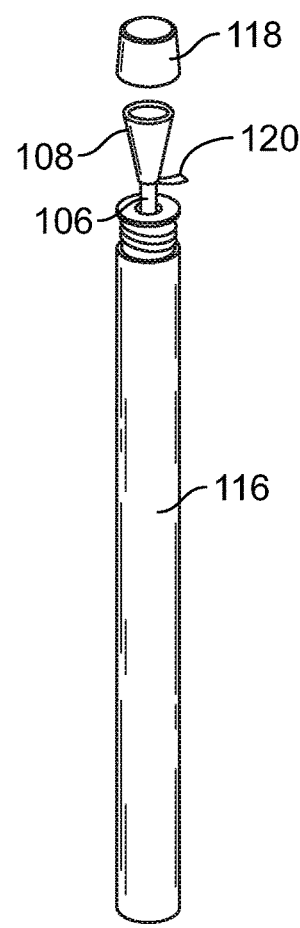
FIG. 10 is a perspective view of the reusable urinary catheter assembly, partially positioned within a storage container.

FIGS. 8-10 show another embodiment of a reusable urinary catheter assembly 100 according to the present disclosure. The reusable urinary catheter assembly 100 may be provided as either a male catheter assembly or as a female catheter assembly without departing from the scope of the present disclosure.

The reusable urinary catheter assembly 100 of FIGS. 8-10 includes a catheter shaft 102, which may be provided as an elongated, hollow tube extending between a closed proximal end 104 (FIG. 8) and an open distal end 106 (FIG. 10). A drainage member or funnel 108 may be associated with the distal end 106 of the catheter shaft 102, as shown in FIG. 10. The catheter shaft 102 may include one or more drainage eyes or openings 110 at or adjacent to the proximal end 104 of the catheter shaft 102 to drain urine from a bladder into the hollow interior of the catheter shaft 102, where it flows to the drainage member 108 to exit the reusable urinary catheter assembly 100 (as will be described in greater detail).

The reusable urinary catheter assembly 100 is further provided with a plurality of cover layers 112a-112c (FIG. 9) associated with the catheter shaft 102, which provide added functionality that limits the number of times that the reusable urinary catheter assembly 100 may be reused. In particular, the cover layers 112a-112c are arranged from an innermost cover layer 112a (associated with the outer surface of the catheter shaft 102) to an outermost cover layer 112a. It should be understood that FIG. 8 illustrates an outermost cover layer 112c in the process of being removed from the catheter shaft 102, as the cover layers 112a-112c typically lay flat against the catheter shaft 102 or adjacent proximal cover layer. The illustrated embodiment is provided with three cover layers 112a-112c, but it is within the scope of the present disclosure for the reusable urinary catheter assembly 100 to have more or fewer than three cover layers. Preferably, the reusable urinary catheter assembly 100 includes at least two cover layers.

In the illustrated embodiment, the cover layers 112a-112c are concentric and substantially identical, each being shaped to cover and match the contours of the entire outer surface of the catheter shaft 102, although it is within the scope of the present disclosure for one or more of the cover layers to be differently configured from another cover layer. For example, one of the cover layers may be configured to overlay the entire outer surface of the catheter shaft 102, while another cover layer may be configured to overlay a smaller percentage of the catheter shaft 102 (e.g., the distal-most section of the catheter shaft 102, which may be intended to remain outside of the urethra during use).

The illustrated cover layers 112a-112c include apertures or holes 114 aligned with the drainage eyes 110 of the catheter shaft 102 (and aligned with the apertures or holes 114 of the other cover layers 112a-112c) to allow for urine to drain from a bladder into the hollow interior of the catheter shaft 102 via the drainage eyes 110, but it is also within the scope of the present disclosure for one or more of the cover layers 112a-112c to omit such apertures or holes 114. If apertures or holes are omitted from one of the cover layers 112a-112c, it may be advantageous for that cover layer to include in place of an aperture/hole some other means for allowing fluid flow through the cover layer and into the hollow interior of the catheter shaft 102. For example, a cover layer may be provided with a mesh or screen configured to overlay a drainage eye 110 or with a section having a plurality of relatively small openings (e.g., pinholes) configured to overlay a drainage eye 110 to allow fluid flow through the cover layer and into the hollow interior of the catheter shaft 102 via the associated drainage eye 110.

Regardless of the exact number of cover layers and their shapes, it may be preferred for each cover layer to be formed of a film material that is sufficiently thin so as to not significantly increase the effective outer diameter of the catheter shaft 102, while also being sufficiently flexible so as to not significantly affect the flexibility of the catheter shaft 102. More preferably, each cover layer is formed of a material or includes a surface treatment that, when contacted by a lubricating fluid (e.g., water and sterilization fluid) becomes lubricious to allow for improved passage of the covered catheter shaft 102 through a urethra. If the reusable urinary catheter assembly 100 is so configured, a lubricating fluid may be applied to the outermost cover layer in any manner without departing from the scope of the present disclosure, but in the illustrated embodiment, there is provided a lubricating and/or sterilizing fluid-containing storage container 116 (FIG. 10) in which the reusable urinary catheter assembly 100 may be stored between consecutive uses. The storage container 116 may be provided with a removable lid 118 to selectively close and open an open end of the storage container 116 to insert and remove the reusable urinary catheter assembly 100. In a preferred embodiment, the lubricating fluid is water, with at least a portion of each cover layer being provided with a hydrophilic coating that, when contacted by water in the storage container 116, results in a lubricious surface for the outermost cover layer.

Preferably, all of the cover layers 112a-112c are removable members, which may be removed from the catheter shaft 102, although it is within the scope of the present disclosure for one or more of the cover layers (e.g., the innermost cover layer 112a) to be non-removable. It may also be preferred for the removable cover layers to be configured to be individually removed, although it is also within the scope of the present disclosure for the removable cover layers to be configured such that multiple cover layers are removed simultaneously.

In one embodiment, one or more removable cover layers may be provided with a pull tab or gripping formation or member 120 (FIG. 10) associated with the distal end of the cover layer, adjacent to the drainage member 108 (if provided). The pull tab 120 may be formed of a different material than the remainder of the associated cover layer or otherwise be configured to remain non-lubricious when contacted by a lubricating fluid for improved gripping of the pull tab 120. If a removable cover layer is provided with such a pull tab 120, the pull tab 120 may be gripped and manipulated to remove the associated cover layer from the catheter shaft 102. The exact way in which the pull tab 120 is manipulated to remove the associated cover layer may vary without departing from the scope of the present disclosure. For example, in one embodiment, the cover layer may include a frangible section (e.g., a tear line) configured to break when a generally radially directed pulling force is applied to the pull tab 120. In such a configuration, the pull tab 120 is gripped and pulled away from the catheter shaft 102 in a generally radial direction to apply sufficient force to the frangible section so as to break the frangible section and free the cover layer from the catheter shaft 102 or underlying cover layer. Preferably, the frangible section is positioned opposite the pull tab 120, which allows the pull tab 120 to be pulled radially away from the catheter shaft 102 in a manner that applies the maximum amount of force to the frangible section, thereby making it easier for a user to remove the cover layer from the catheter shaft 102.

According to another approach, the cover layer may be provided with a generally helical frangible section or tear line, in which case the pull tab 120 may be pulled in a generally tangential direction to first break the frangible section. Thereafter, the pull tab 120 may be rotated about the catheter shaft 102 to break the remainder of the frangible section and ultimately remove the cover layer from the catheter shaft 102 or underlying cover layer. In yet another embodiment, a frangible section or tear line may be omitted, with the pull tab 120 being gripped and moved in a proximal direction, parallel to the central axis of the catheter shaft 102, to unroll the associated cover layer from the catheter shaft 102 or underlying cover layer.

It should be understood that the foregoing are merely exemplary approaches to removing a cover layer from the catheter shaft 102 and that other approaches to removing a cover layer may be practiced without departing from the scope of the present disclosure. Furthermore, it is within the scope of the present disclosure for different removable cover layers of the same reusable urinary catheter assembly 100 to be differently configured and to be removed by different mechanisms, although it may be preferred for all of the removable cover layers of the same reusable urinary catheter assembly 100 to be similarly configured and removed by the same mechanism. Additionally, it is within the scope of the present disclosure for each removable cover layer of the same reusable urinary catheter assembly 100 to be configured to be removed either using substantially the same amount of force or with differing amounts of force (e.g., with the outermost cover layer 112c being configured to be removed at a lower level of force than the adjacent inner cover layer 112b).

In use, a user may begin by removing the reusable urinary catheter assembly 100 from a sealed package (if provided). With the reusable urinary catheter assembly 100 outside of the package, the user may apply a lubricating fluid to the catheter shaft 102, thereby lubricating at least a portion of the outer surface of the outermost cover layer 112c. This may be done in any of a number of suitable ways (e.g., placing the reusable urinary catheter assembly 100 into the lubricating and/or sterilizing fluid-containing storage container 116) and may alternatively be achieved by providing a pre-lubricated outermost cover layer 112c. With the outermost cover layer 112c suitably lubricated, the user may then grip the drainage member 108 and use it to orient the proximal end 104 of the catheter shaft 102 adjacent to the urethral opening.

In one embodiment, the proximal end 104 of the catheter shaft 102 may be provided with an introducer tip which, if provided, may be used to advance the proximal end 104 of the catheter shaft 102 into the urethra as described above with respect to the embodiment of FIGS. 1-6. The introducer tip may be variously configured without departing from the scope of the present disclosure. For example, in one embodiment, the introducer tip may be of the type illustrated in FIG. 4, with the introducer tip being a reusable, injection-molded component that is used in conjunction with the reusable catheter assembly 100 and storage container 116. In another embodiment, the introducer tip may be a protective sleeve tip that is configured to be incorporated with the cover layers 112a-112c.

The user continues advancing the proximal end 104 of the catheter shaft 102 (and the proximal ends of any cover layers associated with the catheter shaft 102) through the urethra until the proximal end 104 of the catheter shaft 102 is positioned within the bladder, with at least the drainage member 108 positioned outside of the urethra. So positioning the reusable urinary catheter assembly 100 causes urine in the bladder to drain into the catheter shaft 102 via the drainage eye(s) 110. The urine flows from the proximal end 104 of the catheter shaft 102, through the hollow interior, and to the distal end 106 of the catheter shaft 102. The urine flows from the distal end 106 of the catheter shaft 102 and into the drainage member 108, where it exits the reusable urinary catheter assembly 100. The urine may be directed into a toilet or other waste receptacle (e.g., a waste bag secured to or otherwise associated with the drainage member 108).

After the reusable urinary catheter assembly 100 has been used to drain urine from the bladder, the user may grip the drainage member 108 and move it distally away from the body to withdraw the catheter shaft 102 from the urethra. The reusable urinary catheter assembly 100 may then be re-sterilized or otherwise reconditioned for reuse by removing the outermost cover layer, as described above, with the adjacent inner cover layer becoming the new, sterile outermost cover layer. Prior to a second use of the reusable urinary catheter assembly 100, the outermost cover layer may be manipulated to increase its lubricity, if necessary (as described above). The steps of using the reusable urinary catheter assembly 100 for catheterization and re-sterilization or reconditioning of the reusable urinary catheter assembly 100 by removal of one or more of the removable cover layers may be repeated until the final removable cover layer is removed. The reusable urinary catheter assembly 100 may be configured such that, when the final removable cover layer has been removed, the reusable urinary catheter assembly 100 may be used one last time before being replaced with another reusable urinary catheter assembly. Alternatively, the reusable urinary catheter assembly 100 may be configured such that, when the final removable cover layer has been removed, the reusable urinary catheter assembly 100 is no longer in condition for reuse or is otherwise ready for replacement with another reusable urinary catheter assembly.

Finally, the reusable urinary catheter assembly 100 may be disposed of (e.g., placed into a toilet if it is formed of a water-degradable material or otherwise placed into a garbage receptacle).

According to a preferred embodiment, between first and second uses of the reusable urinary catheter assembly 100, the reusable urinary catheter assembly 100 is re-sterilized by removing the outermost cover layer 112c and placing the reusable urinary catheter assembly 100 into a storage container 116 (FIG. 10) containing an amount of a lubricating and/or sterilizing fluid, as described above. When the reusable urinary catheter assembly 100 is to be used a second time, the lid 118 is removed from the storage container 116 and then the reusable urinary catheter assembly 100 is removed from the storage container 116, with the new outermost cover layer 112b having been lubricated by the lubricating fluid in the storage container 116. In one embodiment, the lubricating fluid may also serve to sterilize the reusable urinary catheter assembly 100 between uses, but it is also within the scope of the present disclosure for alternative sterilization approaches (e.g., steam sterilization using an autoclave or the like) to be employed.

After using the reusable urinary catheter assembly 100 a second time, it is re-sterilized or reconditioned for use by removing outermost cover layer 112b (as described above), leaving only the innermost cover layer 112a. The reusable urinary catheter assembly 100 may then be used a third time for catheterization (as described above). In one embodiment, the innermost cover layer 112a is fixedly secured to the catheter shaft 102a, such that a user attempting to remove the innermost cover layer 112a will find it to be impossible, thereby signaling the need for a replacement reusable urinary catheter assembly. Alternatively, the innermost cover layer 112a may be removed to expose the catheter shaft 102, which may similarly signal the need for a replacement reusable urinary catheter assembly. Thus, it will be seen that the number of times that the reusable urinary catheter assembly 100 may be reused is limited by the number of removable cover layers. The number of times that a reusable urinary catheter assembly may be reused may be varied by providing it with differing numbers of removable members.

It should be understood that the illustrated embodiment of FIGS. 8-10 is merely exemplary and that variations to that design may be made without departing from the scope of the present disclosure. For example, in one embodiment the cover layers may be differently colored than the catheter shaft to better signal to a user that it is necessary to replace the reusable urinary catheter assembly when the differently colored catheter shaft has been exposed. In another embodiment, text may be provided on the cover layers and/or the catheter shaft to inform the user of the number of times that the reusable urinary catheter assembly may be reused and/or to alert the user that the reusable urinary catheter assembly must be replace. The cover layers may be differently colored and/or numbered, for example, to initiate and guide use and to differentiate the various cover layers. Other variations to the configuration of the reusable urinary catheter assembly and associated components (e.g., the storage container and lid) may also be practiced without departing from the scope of the present disclosure.

Aspects of the present subject matter described above may be beneficial alone or in combination with one or more other aspects. Without limiting the foregoing description, in accordance with one aspect of the subject matter herein, there is provided a reusable urinary catheter assembly, which includes a catheter shaft and a plurality of removable members associated with the catheter shaft. A different one of the removable members is configured to be removed from the catheter shaft between each consecutive use of the reusable urinary catheter assembly, with the number of times that the reusable urinary catheter assembly me be reused being limited by the number of removable members.

In accordance with another aspect which may be used or combined with the preceding aspect, one of the removable members is a final removable member that, when removed from the catheter shaft, prevents further reuse of the reusable urinary catheter assembly.

In accordance with another aspect which may be used or combined with the first aspect, one of the removable members is a final removable member that, when removed from the catheter shaft, allows for one more use of the reusable urinary catheter assembly.

In accordance with another aspect which may be used or combined with any of the preceding aspects, the removable members are arranged from a proximal-most removable member to a distal-most removable member.

In accordance with another aspect which may be used or combined with any of the first through fourth aspects, the urinary catheter shaft has an outer surface, with the removable members being arranged from an innermost removable member associated with the outer surface of the catheter shaft to an outermost removable member.

In accordance with another aspect which may be used or combined with any of the preceding aspects, the removable members are substantially identical.

In accordance with another aspect which may be used or combined with any of the preceding aspects, the force required to remove at least two of the removable members is different.

In accordance with another aspect which may be used or combined with any of the first through sixth aspects, the force required to remove each of the removable members is different.

In accordance with another aspect which may be used or combined with any of the first through sixth aspects, the force required to remove each of the removable members is substantially the same.

In accordance with another aspect, there is provided a method for using a reusable urinary catheter assembly. The method includes using a reusable urinary catheter assembly for catheterization, removing a removable member from the reusable urinary catheter assembly, and reusing the reusable urinary catheter assembly for catheterization. The number of times that the reusable urinary catheter assembly may be reused is limited by the number of removable members associated with it.

In accordance with another aspect which may be used or combined with the immediately preceding aspect, removing a removable member from the reusable urinary catheter assembly includes removing a distal-most removable member from the reusable urinary catheter assembly.

In accordance with another aspect which may be used or combined with the tenth aspect, removing a removable member from the reusable urinary catheter assembly includes removing an outermost removable member from the reusable urinary catheter assembly.

In accordance with another aspect which may be used or combined with any of the preceding three aspects, a final removable member is removed from the reusable urinary catheter assembly, thereby preventing further reuse of the reusable urinary catheter assembly.

In accordance with another aspect which may be used or combined with any of the tenth through twelfth aspects, a final removable member is removed from the reusable urinary catheter assembly, thereby allowing for one more use of the reusable urinary catheter assembly.

In accordance with another aspect which may be used or combined with any of the preceding five aspects, removing a removable member from the reusable urinary catheter assembly includes applying a different amount of force to remove at least two of the removable members.

In accordance with another aspect which may be used or combined with any of the tenth through fourteenth aspects, removing a removable member from the reusable urinary catheter assembly includes applying a different amount of force to remove each of the removable members.

In accordance with another aspect which may be used or combined with any of the tenth through fourteenth aspects, removing a removable member from the reusable urinary catheter assembly includes applying substantially the same amount of force to remove each of the removable members.

In accordance with another aspect, there is provided a reusable urinary catheter assembly, which includes a catheter shaft extending between proximal and distal ends. The method reusable urinary catheter assembly also includes a frangible drainage member associated with the distal end of the catheter shaft. The frangible drainage member includes a plurality of segments, which are arranged from a proximal-most segment to a distal-most segment, with at least the distal-most segment being a removable member configured to be removed from the catheter shaft between consecutive uses of the reusable urinary catheter assembly.

In accordance with another aspect which may be used or combined with the immediately preceding aspect, the segments are substantially identical.

In accordance with another aspect which may be used or combined with any of the preceding two aspects, the segments are generally frusto-conical.

In accordance with another aspect which may be used or combined with any of the preceding three aspects, at least two of the segments are removable members.

In accordance with another aspect which may be used or combined with the twenty-first aspect, the force required to remove each of the removable members is greater than the force required to remove any removable members positioned distally thereof.

In accordance with another aspect which may be used or combined with any of the preceding five aspects, the proximal-most segment is fixedly secured to the catheter shaft and all of the other segments are removable members.

In accordance with another aspect which may be used or combined with any of the preceding six aspects, there is provided a storage container including a lid defining a cavity configured to receive at least one of the segments upon distal movement of the frangible drainage member into the cavity, with at least one of the segments being configured to be removed from the catheter shaft upon proximal movement of the catheter shaft away from the lid.

In accordance with another aspect which may be used or combined with the immediately preceding aspect, the proximal-most segment is fixedly secured to the catheter shaft so as to be irremovable from the cavity of the lid when the proximal-most segment is positioned within the cavity of the lid, thereby preventing further reuse of the reusable urinary catheter assembly.

In accordance with another aspect which may be used or combined with any of the eighteenth through twenty-third aspects, there is provided a storage container including a lid defining a plurality of cavities. The number of cavities is equal to the number of segments, with each cavity being configured to receive one of the segments upon distal movement of the frangible drainage member into the cavity. All but the proximal-most segment is configured to be removed from the catheter shaft upon movement of the catheter shaft away from the lid.

In accordance with another aspect, there is provided a reusable urinary catheter assembly, which includes a catheter shaft having an outer surface. The method reusable urinary catheter assembly also includes a plurality of concentric cover layers arranged from an innermost cover layer associated with the outer surface of the catheter shaft to an outermost cover layer, with at least the outermost cover layer being a removable member configured to be removed from the catheter shaft between consecutive uses of the reusable urinary catheter assembly.

In accordance with another aspect which may be used or combined with the immediately preceding aspect, the cover layers are substantially identical.

In accordance with another aspect which may be used or combined with any of the preceding two aspects, at least one of the cover layers includes a pull tab.

In accordance with another aspect which may be used or combined with any of the preceding three aspects, the cover layers are a different color than the catheter shaft.

In accordance with another aspect which may be used or combined with any of the preceding four aspects, the catheter shaft extends between proximal and distal ends. Each cover layers extends between the proximal and distal ends of the catheter shaft.

In accordance with another aspect which may be used or combined with any of the preceding five aspects, the catheter shaft extends between proximal and distal ends. A drainage eye is defined in the catheter shaft adjacent to the proximal end of the catheter shaft, with each cover layer defining an opening at least substantially aligned with the drainage eye In accordance with another aspect which may be used or combined with any of the preceding six aspects, each of the cover layers is a removable member.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A reusable urinary catheter assembly, comprising:
   a catheter shaft; and
   a plurality of removable members associated with the catheter shaft, wherein
     a different one of said removable members is configured to be removed from the catheter shaft between each consecutive use of the reusable urinary catheter assembly, and
     the number of times that the reusable urinary catheter assembly may be reused is limited by the number of removable members.

2. The reusable urinary catheter assembly of claim 1, wherein the removable members are arranged from a proximal-most removable member to a distal-most removable member.

3. The reusable urinary catheter assembly of claim 1, wherein
   the urinary catheter shaft includes an outer surface, and
   the removable members are arranged from an innermost removable member associated with the outer surface of the catheter shaft to an outermost removable member.

4. The reusable urinary catheter assembly of claim 1, wherein the removable members are substantially identical.

5. The reusable urinary catheter assembly of claim 1, wherein the force required to remove each of said removable members is substantially the same.

6. A method of using a reusable urinary catheter assembly, comprising:
   (a) using a reusable urinary catheter assembly for catheterization;
   (b) removing a removable member from the reusable urinary catheter assembly;
   (c) reusing the reusable urinary catheter assembly for catheterization; and
   (d) repeating (b) and (c), wherein the number of times that (b) and (c) may be repeated is limited by the number of removable members associated with the reusable urinary catheter assembly.

7. The method of claim 6, wherein said removing a removable member from the reusable urinary catheter assembly includes removing a distal-most removable member from the reusable urinary catheter assembly.

8. The method of claim 6, wherein said removing a removable member from the reusable urinary catheter assembly includes removing an outermost removable member from the reusable urinary catheter assembly.

9. The method of claim 6, wherein removing a removable member from the reusable urinary catheter assembly includes applying a different amount of force to remove at least two of the removable members.

10. The reusable urinary catheter assembly of claim 1, wherein
    the catheter shaft extends between proximal and distal ends, and
    the plurality of removable members comprise a plurality of segments of a frangible drainage member associated with the distal end of the catheter shaft.

11. The reusable urinary catheter assembly of claim 10, wherein the segments are generally frusto-conical.

12. The reusable urinary catheter assembly of claim 10, wherein the force required to remove each of said removable members is greater than the force required to remove any removable members positioned distally thereof.

13. The reusable urinary catheter assembly of claim 10, wherein the proximal-most segment is fixedly secured to the catheter shaft and all of the other segments comprise removable members.

14. The reusable urinary catheter assembly of claim 10, further comprising a storage container including a lid defining a cavity configured to receive at least one of said segments upon distal movement of the frangible drainage member into the cavity, wherein said at least one of said segments is configured to be removed from the catheter shaft upon proximal movement of the catheter shaft away from the lid.

15. The reusable urinary catheter assembly of claim 14, wherein the proximal-most segment is fixedly secured to the catheter shaft so as to be irremovable from the cavity of the lid when the proximal-most segment is positioned within the cavity of the lid, thereby preventing further reuse of the reusable urinary catheter assembly.

16. The reusable urinary catheter assembly of claim 10, further comprising a storage container including a lid defining a plurality of cavities, wherein
    the number of cavities is equal to the number of segments,
    each cavity is configured to receive one of said segments upon distal movement of the frangible drainage member into the cavity, and
    all but the proximal-most segment is configured to be removed from the catheter shaft upon proximal movement of the catheter shaft away from the lid.

17. The reusable urinary catheter assembly of claim 1, wherein
    the catheter shaft includes an outer surface, and
    the plurality of removable members comprise a plurality of concentric cover layers arranged from an innermost cover layer associated with the outer surface of the catheter shaft to an outermost cover layer.

18. The reusable urinary catheter assembly of claim 17, wherein at least one of the cover layers includes a pull tab.

19. The reusable urinary catheter assembly of claim 17, wherein the cover layers are a different color than the catheter shaft.

20. The reusable urinary catheter assembly of claim 17, wherein
    the catheter shaft extends between proximal and distal ends,
    a drainage eye is defined in the catheter shaft adjacent to the proximal end of the catheter shaft, and
    each cover layer defines an opening at least substantially aligned with the drainage eye.

* * * * *